United States Patent [19]
Toki

[11] 3,961,247
[45] June 1, 1976

[54] LINEAR OUTPUT MOISTURE METER WITH TEMPERATURE COMPENSATOR

[75] Inventor: Kuni Toki, Tokyo, Japan

[73] Assignee: Kett Electric Laboratory, Tokyo, Japan

[22] Filed: June 16, 1975

[21] Appl. No.: 587,495

[30] Foreign Application Priority Data
July 19, 1974  Japan.............................. 49-83013

[52] U.S. Cl............................................. 324/65 R
[51] Int. Cl.²...................................... G01R 27/02
[58] Field of Search .............. 324/65 R; 73/362 AR

[56] References Cited
UNITED STATES PATENTS
3,416,076   12/1968   Clinton ........................ 324/65 R X
3,441,846   4/1969    Petrohilos ...................... 324/65 R

*Primary Examiner*—Stanley T. Krawczewicz
*Attorney, Agent, or Firm*—Elliott I. Pollock

[57] ABSTRACT

Apparatus for electrically measuring the water content of a specimen such as grain the electric resistivity of which has a correlation with the water content, comprising a linearizer for converting the measured electric resistivity in the low water content region in which the electric resistivity of a grain specimen changes non-linearly with the water content into an electric quantity linearly changing with the water content, and a temperature compensator including a temperature sensitive element for generating a linearly changing electric signal with temperature, the temperature compensator generating a temperature-compensating electric signal from said linearly changing temperature signal, the temperature compensation of the measured value being commonly done with said temperature compensator in both the low and the high water content ranges by adding a linearly changing electric quantity corresponding to the measured water content and the compensating electric signal.

6 Claims, 3 Drawing Figures

LINEAR OUTPUT MOISTURE METER WITH TEMPERATURE COMPENSATOR

BACKGROUND OF THE INVENTION

1. Field of the Invention

This invention relates to a moisture meter for measuring the water content in a specimen through measuring the electric resistance of the specimen, and more particularly to such a moisture meter provided with temperature compensation.

Description of the Prior Art

In grains such as rice or wheat, the water content was a correlation with the electric resistivity and hence it can be discovered by measuring the electric resistivity.

The electric resistivity of grain with a constant water content, however, shows a temperature dependence corresponding to the water content of ± 1.0% for the temperature change of ± 10°C. Thus, temperature compensation should be done in measuring the water content of a grain specimen from the electric resistivity. It has been done by compensating the measured result with a temperature compensation table, or with a compensating quantity which is arranged to be directly read from a thermometer. "Grain moisture meter, model SP-1" (since April, 1967) of Kett Electric Laboratory in Japan and "moisture meter, model TW73" (trade name "Protimeter Grain-master") (Since 1973) of Protimeter Ltd. are examples of these types.

According to such methods, however, temperature compensation is troublesome and time-consuming.

It has been known that at a constant temperature the electric resistivity of grain varies with the water content as is shown in FIG. 1, i.e. it varies exponentially in the water content range of 12 to 20% and relatively linearly in the water content range of 20 30%. However, in performing such a method with one range of reading, there occur problems of making the circuit structure extremely complicated and the adjustment of the circuit extremely difficult, thereby bringing it into practice being difficult. Thus, it can be considered to divide the whole range into a low water content range of 12 to 20% and a high water content range of 20 to 30%.

As an attempt in linearizing the indication scale in a moisture meter, Japanese Patent Publication No. 35039/1973 discloses such an electric resistance measuring apparatus in that an electric signal is amplified in an amplifying transistor in the low water content range in which it was difficult to measure fine differences in the water content because of its high resistivity, an electric signal is by-passed through a compensating transistor used in diode-like manner in the high water content range to decrease the rate of change, and the water content is preliminarily converted into the current flowing through a reference resistance and indicated in a meter to enable direct reading. In this apparatus, however, no consideration is made of the temperature compensation which is indispensable in the water content measurement of grain specimens.

SUMMARY OF THE INVENTION

This invention is made on review of these conventional techniques and intended to eliminate the drawbacks thereof.

An object of this invention is to provide a moisture meter capable of automatic temperature compensation in the measurement of the water content in specimens with a simple circuit structure, of easy and highly accurate measurement of the water content in specimens, and of being easily brought into practical use.

According to this invention, the electric resistivity of a specimen is measured to know the water content in the specimen which has a correlation with the electric resistivity. Measurement of the water content in a specimen in the low water content range in which the electric resistivity changes nonlinearly with the water content is done through a linearizer. Temperature compensation of the measurement is done by a common temperature compensator in both the low and the high water content ranges. Thus, the temperature compensation for the water content in specimens can be done automatically with a simple circuit structure, and measurement of the water content in specimens can be done easily and accurately. Further, the moisture meter according to this invention can be easily brought into practical use.

Other objects, features and advantages of this invention will become apparent from the following detailed description when taken in conjunction with the accompanying drawings.

DESCRIPTION OF THE PREFERRED EMBODIMENTS

Figure 1:
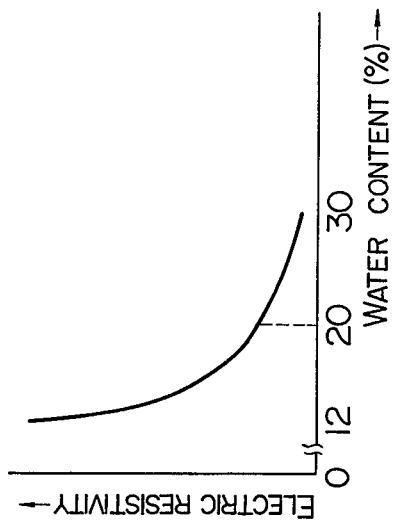
FIG. 1 is a graph showing the relation of the water content and the electric resistivity in grain at a constant temperature.
Figure 2:
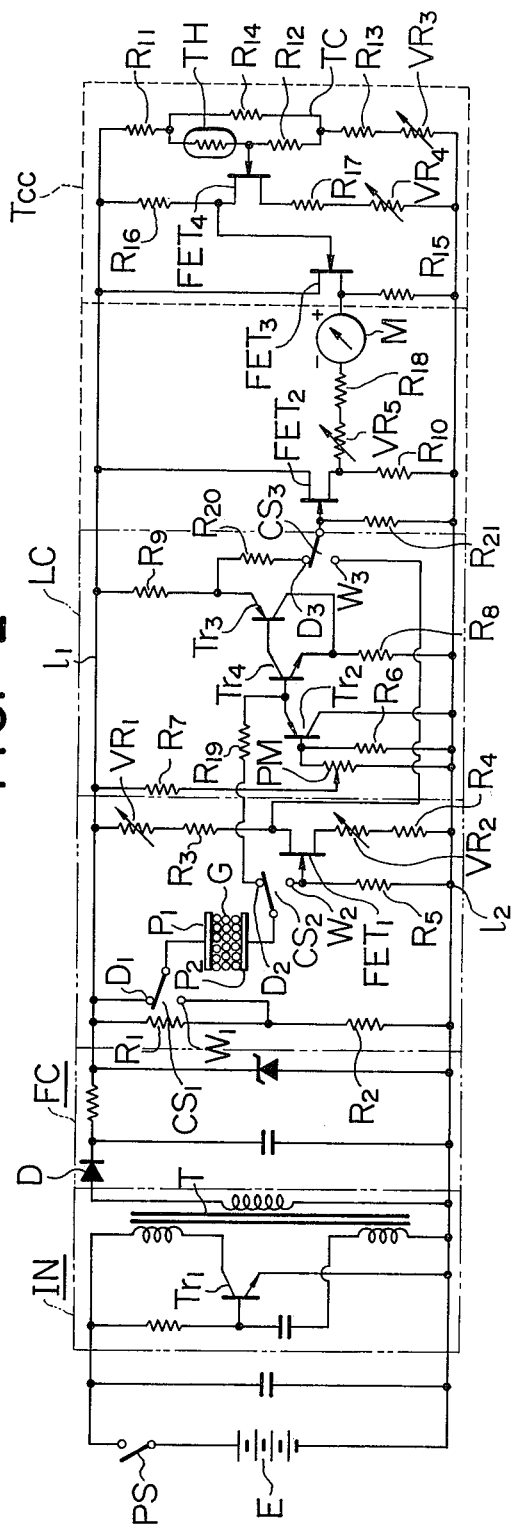
FIG. 2 is a circuit diagram of an embodiment of the moisture meter according to this invention.

An embodiment of the moisture meter according to this invention is shown in FIG. 2. A dc power source E, e.g. 6V, such as a battery is connected through a power switch PS to an inverter circuit IN including a first transistor $Tr_1$ of NPN type and an inverter transformer T. The output of the inverter circuit IN is rectified and smoothed in a rectifying diode D and a smoothing circuit FC. Thus, a low dc voltage, e.g. 6V, from said dc power source E is converted to a relatively high dc voltage, e.g. 20V or above. Lines $l_1$ and $l_2$ are connected to the positive and the negative terminals of said smoothing circuit FC. Between the lines $l_1$ and $l_2$ are connected a voltage dividing series circuit formed of resistors $R_1$ and $R_2$ and a first field effect transistor $FET_1$ of N-channel type having a drain connected to the line $l_1$ through a series circuit of a resistor $R_3$ and a first variable resistor $VR_1$ and a source to the line $l_2$ through a series circuit of a second variable resistor $VR_2$ and a resistor $R_4$, a linearizer LC comprising a second and a third transistors $Tr_2$ and $Tr_3$ of PNP type, and a fourth transistor $Tr_4$ of NPN type, in which the transistor $Tr_3$ and $Tr_4$ are complementally connected. In said linearizer LC, the second transistor $Tr_2$ has an emitter connected to a base of the fourth transistor $Tr_4$, a collector to the line $l_2$, and a base to the line $l_2$ through a parallel circuit of a resistor $R_6$ and a potentiometer PM and to the line $l_1$ through the movable terminal of the potentiometer PM and a resistor $R_7$ in series connection. The fourth transistor $Tr_4$ has a collector connected to the base of the third transistor $Tr_3$, an emitter to the collector of the third transistor $Tr_3$ and the line $l_2$ through a resistor $R_8$. The third transistor $Tr_3$ has an emitter connected to the line $l_1$ through a resistor $R_9$. A resistor $R_5$ is connected between the gate of the first field effect transistor $FET_1$ and the line $l_2$. Further, between the lines $l_1$ and $l_2$ are connected a second field effect transistor $FET_2$ of N-channel having a source connected to the line $l_2$ through a resistor $R_{10}$, and a temperature compensating circuit TCC including a third and a fourth field effect transistor $FET_3$ and $FET_4$ of N-channel and a temperature detecting circuit TC having a thermistor TH of negative characteristic (its resistance decreases with an increase in temperature) for detecting the temperature of a grain specimen to be described later. In the temperature detecting circuit TC, the thermistor TH has one end connected to the line $l_1$ through a resistor $R_{11}$ and the other end to the line $l_2$ through resistors $R_{12}$ and $R_{13}$ and a third variable resistor $VR_3$ connected in series, and a resistor $R_{14}$ is connected in parallel with the series connection of the thermistor TH and the resistor $R_{12}$. In the temperature compensating circuit TCC, the third field effect transistor $FET_3$ has a drain connected to the line $l_1$, a source to the line $l_2$ through a resistor $R_{15}$, and a gate to the drain of the fourth field effect transistor $FET_4$. Further, the fourth field effect transistor $FET_4$ has a drain connected to the line $l_1$ through a resistor $R_{16}$, a source to the line $l_2$ through a series connection of a resistor $R_{17}$ and a fourth variable resistor $VR_4$, and a gate to the interconnection point of the thermistor TH and the resistor $R_{12}$. The second field effect transistor $FET_2$ has a gate connected to the line $l_2$ through a resistor $R_{21}$ and to a change-over switch $CS_3$, a drain connected to the line $l_1$, and a source connected to the line $l_2$ through resistor $R_{10}$. Between the sources of the second and the third field effect transistors $FET_2$ and $FET_3$ is connected a series connection of a fifth variable resistor $VR_5$, a resistor $R_{18}$ and a water content meter M. A pair of electrodes $P_1$ and $P_2$ are provided. One electrode $P_1$ is connected to the line $l_1$ through a "dry" contact $D_1$ of a first changeover switch $CS_1$ and to the interconnection point of the resistors $R_1$ and $R_2$ through a "wet" contact $W_1$ of the change-over switch $CS_1$, and the other electrode $P_2$ to the emitter of the second transistor $Tr_2$ through a series connection of a "dry" contact $D_2$ of a second change-over switch $CS_2$ and a resistor $R_{19}$ and to the gate of the first field effect transistor $FET_1$ through a "wet" contact $W_2$ of the second change-over switch $CS_2$. Further, the gate of the second field effect transistor $FET_2$ is connected to the emitter of the third transistor $Tr_3$ through a series connection of a dry contact $D_3$ of a third change-over switch $CS_3$ and a resistor $R_{20}$, and to the drain of the first field effect transistor $FET_1$ through a wet contact $W_3$ of the third change-over switch $CS_3$. Here, the respective change-over switches $CS_1$, $CS_2$ and $CS_3$ are mutually interlocked so that the on-off operation of the dry contacts $D_1$, $D_2$ and $D_3$ and the wet contacts $W_1$, $W_2$ and $W_3$ are respectively synchronous. A grain specimen G such as rice or wheat is disposed between the electrodes $P_1$ and $P_2$. Here, an ammeter is used as the water content measuring meter M, in which a current scale is replaced with a corresponding water content scale.

In the above circuit, when the water content of a grain specimen G is in the low water content range of 12 to 20%, the wet contacts $W_1$, $W_2$ and $W_3$ of the respective change-over switch $CS_1$, $CS_2$ and $CS_3$ are opened and the dry contact $D_1$, $D_2$ and $D_3$ are closed to interpose the linearizer LC between the electrode $P_2$ and the gate of the second field effect transistor $FET_2$. In this state, when the power switch PS is thrown in, the emitter potential of the second transistor $Tr_2$, i.e. the base potential of the fourth transistor $Tr_4$ of the linearizer is established according to the electric resistance of the grain specimen G between the two electrodes $P_1$ and $P_2$ and those of the transistors $Tr_2$, $Tr_3$ and $Tr_4$. In a transistor, the collector current varies exponentially with respect to the base-emitter voltage. Thus, the operation characteristics of the transistors $Tr_2$, $Tr_3$ and $Tr_4$ can be predetermined to generate an electric signal output changing linearly with the water content in the grain specimen G from the exponential variation of the resistivity of the grain specimen G with the water content. Thus, the linearizer LC generates an output signal changing linearly with the water content. The output of the linearizer LC, i.e. the emitter output of the third transistor $Tr_3$ is supplied to the gate of the second field effect transistor $FET_2$ which has a linear gate-source voltage vs. drain current characteristic. Hence, the second field effect transistor $FET_2$ controls the drain current in proportion to the water content of the grain specimen G and changes the source potential linearly with the water content of the grain specimen G. As a result, the current flowing through the meter M varies linearly with the water content of the grain specimen G, and the needle of the meter M moves linearly thereby.

When the water content of a grain specimen is in the high water content range of 20 to 30%, the dry contacts $D_1$, $D_2$ and $D_3$ of the respective change-over switches $Cs_1$, $CS_2$ and $CS_3$ are opened and the wet contacts $W_1$, $W_2$ and $W_3$ thereof are closed to interpose the first field effect transistor $FET_1$ between the electrode $P_2$ and the gate of the second field effect transistor $FET_2$. When the power switch PS is thrown in this state, the gate potential of the first field effect transistor $FET_1$ is established in accordance with the electric resistance of the grain specimen G between the electrodes $P_1$ and $P_2$ to activate the transistor $FET_1$ accordingly. Here, the field effect transistor changes the drain current linearly with the gate-source voltage. Thus, the linear change of the electric resistivity with the water content in the grain specimen produces a corresponding linear change of the drain output of the first field effect transistor $FET_1$. As the drain output of the first field effect transistor $FET_1$ is applied to the gate of the second field effect transistor $FET_2$, the second field effect transistor $FET_2$ controls the drain current in proportion to the water content of the grain G and changes the source potential linearly therewith, similar to the case of the low water content range. In this case also, the current flowing through the meter M varies linearly with the water content of the grain specimen G and the needle in the meter M moves linearly thereby.

Therefore, it is possible by the adjustment of the first, the second and the fifth variable resistors $VR_1$, $VR_2$ and $VR_5$ and potentiometer PM to arrange the linear movement of the needle in the meter G in both the low and the high water content ranges and the water content scale with equal gaps. Thus, reading of the meter G is made easy.

On the other hand, in the temperature compensator TCC, the resistance of the thermistor TH varies according to the temperature of the grain specimen G and the gate potential of the fourth field effect transistor $FET_4$ is changed thereby. The drain output of the fourth field effect transistor $FET_4$ controlled by the resistance of the thermistor settles the gate potential of the third field effect transistor $FET_3$ to control it accordingly. Here, the resistance of the thermistor TH does not necessarily change linearly with the temperature, but the gate potential of the fourth field effect transistor $FET_4$ can be predetermined to change substantially linearly with the temperature of the grain G. The field effect transistors $FET_3$ and $FET_4$ provide drain currents changing linearly with the gate-source voltages. Thus, the source voltage of the third field effect transistor $FET_3$ changes linearly with the temperature of the grain G. Namely, the temperature compensator TCC linearly controls the current flowing through the water content meter M with respect to the temperature of the grain specimen G.

Thus, when the circuit is so arranged that the changes in the output of the temperature compensator TCC (the source voltage of the third field effect transistor $FET_3$) compensates the changes in the source voltage of the second field effect transistor $FET_2$ due to the temperature variation, the current flowing through the water content meter M does not change with the temperature of the grain specimen G but only with the water content of the grain specimen G. Therefore, the meter G can indicate the true water content of the grain G.

As is described above, the water content of a grain specimen is measured by measuring the electric resistance of the grain specimen through a linearizer in the low water content range and directly in the high water content range, and thereby the water content of the grain can be read out with temperature-compensation throughout the low and the high water content ranges by a common temperature compensator.

Therefore, the temperature compensation for the water content of grain specimens can be done automatically with a simple circuit structure and the water content of grain specimens can be measured easily and highly accurately.

Figure 3:
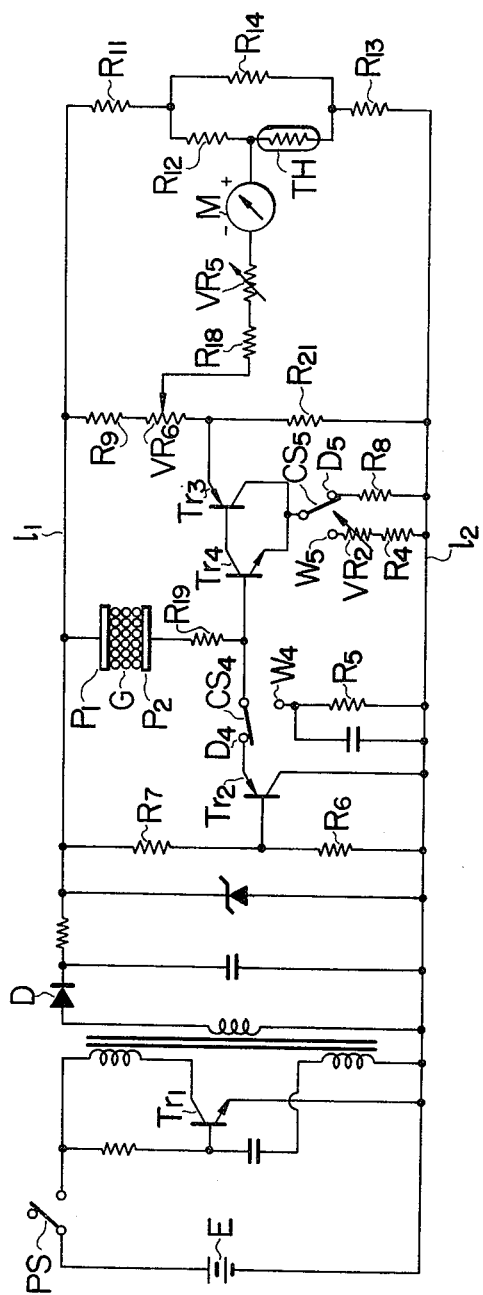
FIG. 3 is a circuit diagram of another embodiment of the moisture meter according to this invention.

A simplified embodiment of the moisture meter according to this invention is shown in FIG. 3, in which similar parts with those of FIG. 2 are indicated by similar reference marks. In this circuit, a changeover switch $CS_5$ is provided at the interconnection point of the emitter of a fourth transistor $Tr_4$ and the collector of a third transistor $Tr_3$. A wet contact $W_5$ of the switch $CS_5$ is connected to a line $l_2$ through a biasing series connection of a resistor $R_4$ and a variable resistor $VR_2$, and a dry contact $D_5$ thereof to the line $l_2$ through a resistor $R_8$. The emitter of the third transistor $Tr_3$ is connected to the line $l_1$ through a potentiometer $VR_6$ and a resistor $R_9$ and to the line $l_2$ through a resistor $R_{21}$. The moving contact of the potentiometer $VR_6$ is connected to a meter M through a series connection of a resistor $R_{18}$ and a variable resistor $VR_5$. The base of the fourth transistor $Tr_4$ is connected to an electrode $P_2$ through a resistor $R_{19}$. The other electrode $P_1$ is connected to the line $l_1$. The interconnection point of a voltage dividing circuit consisting of resistors $R_6$ and $R_7$ is connected to the base of a second transistor $Tr_2$ of PNP type. The collector of the transistor $Tr_2$ is connected to the line $l_2$. A change-over switch $CS_4$ is provided at the interconnection point of the resistor $R_{19}$ and the base of the fourth transistor $Tr_4$, and has a dry contact $D_4$ connected to the emitter of the second transistor $Tr_2$ and a wet contact connected to the line $l_2$ through a parallel circuit of a capacitor and a resistor $R_5$. The change-over switches $CS_4$ and $CS_5$ are interlocked in relation with the selection of the water content range of the specimen. In this embodiment, for the measurement in the high water content range the transistor $Tr_2$ is isolated by the change-over switch $CS_4$ and the emitter resistance for the transistor $Tr_4$ is changed to high by the change-over switch $CS_5$ so as to increase the input impedance for the transistor $Tr_4$ and to change the base potential of the transistor $Tr_4$ linearly with the water content of the grain specimen G. It is apparently possible to provide an appropriate amplifier to linearly amplify the output signal for improving the sensitivity.

In the above embodiments, description of the linearizer was limited to ones including the second, the third, and the fourth transistors. It will be apparent, however, that the linearizer is not limited to the described ones. Further, although the specimen was grain in the above embodiments, it is also apparent that the specimen is not limited to grain. Yet further, it is apparent that the circuit structure of the temperature compensator is not limited to those of the above embodiments.

I claim:

1. A moisture measuring apparatus for measuring the water content of a specimen by measuring the electric resistivity of the specimen which has a correlation with the water content, the electric resistivity of the specimen varies non-linearly with the water content in one water content range and linearly with the water content in another water content range, comprising:
   means for measuring the electric resistivity of said specimen;
   linearizer means for generating an electric signal varying linearly with the water content of the specimen in said one water content range from an electric signal changing non-linearly with the water content;
   indicator means for indicating the measured quantity in terms of the water content;
   change-over means for connecting and disconnecting said linearizer means between said resistivity measuring means and said indicator means; and
   temperature compensating means for measuring the temperature of the specimen and shifting the zero point of the indicator means corresponding to the measured temperature, the linearizer means being so adjusted that the same temperature compensating means provides accurate temperature compensation both for said one and another water content ranges.

2. A moisture measuring apparatus for electrically measuring the water content of a specimen which has a correlation with the electric resistivity of the specimen, comprising:
   means for providing a stabilized d.c. power source of a relatively high voltage;
   means for detecting the electric resistivity of the specimen in the form of an electric quantity by the application of said d.c. voltage through a resistance connected in series to said power source and said specimen, said means including a pair of electrode members disposed so as to contain said specimen and to make pressed contact with said specimen, said specimen having such a property that its electric resistivity varies non-linearly in one water content range and linearly in another water content range with respect to the water content;
   linearizer means including a plurality of active elements and connected to the output terminal of said detecting means through said resistor for converting a non-linearly varying signal from said detecting means into a linearly varying signal;

temperature compensator means including a voltage dividing circuit having a temperature detecting element the resistance of which varies substantially linearly with respect to the temperature of the specimen, for temperature-compensating the water content measurement by varying the voltage dividing ratio according to the detected temperature; and indicating means including another voltage dividing circuit for providing a voltage dividing ratio corresponding to one of the linearly varying detection signal and the linearized detection signal from said detecting means and a water-content-scaled indicator; said another voltage dividing circuit, said indicator and the voltage dividing circuit of said temperature compensator means forming a bridge circuit, and said indicator being connected at the balancing tapping points of said bridge so as to indicate the measured water content.

3. A moisture measuring apparatus according to claim 2, wherein said linearizer means comprises at least a first transistor having an emitter connected to the output terminal of said detecting means, a base connected to a biasing source for determining the rising threshold voltage for operation, and a collector connected to the ground, and a second transistor being complementary to said first transistor and having a base connected to the emitter of said first transistor, and a collector connected to the voltage dividing point of said another voltage dividing circuit of said indicator.

4. A moisture measuring apparatus according to claim 2, wherein the voltage dividing circuit of said temperature compensator means includes a thermistor constituting the temperature detecting element and a plurality of resistance elements connected in series to said thermistor, and connected between the two terminals of said d.c. power source with an adjustable voltage dividing ratio, and said indicator means includes an ammeter having terminals connected between the voltage dividing terminals of said voltage dividing circuits.

5. A moisture measuring apparatus according to claim 2, further comprising a first change-over switch connected between said detector means and said indicator for connecting and disconnecting said linearizer means therebetween, a second change-over switch interlocked with said first change-over switch for changing over the voltage applied to the electrodes of said detecting means corresponding to the selection of said water content ranges, a potentiometer for adjusting the level of the detected signal in said another water content range, and another potentiometer provided in the voltage dividing circuit of said indicator for adjusting the voltage dividing ratio.

6. A moisture measuring apparatus according to claim 2, further comprising a first and a second transistors each having an emitter, a base and a collector in said linearizer means, and a first and a second change-over switches interlocked to each other, said second transistor having the base connected to one of said pair electrodes through a resistor, the collector being the output terminal and connected to the voltage dividing circuit of said indicator, for the measurement in said water content range said first transistor having the emitter connected to the input base of said second transistor through said first change-over switch, the base connected to a bias source for setting the rising threshold point and the collector grounded, said second transistor having the emitter connected to a first biasing means through the second change-over switch thereby linearizing the detected resistance signal, while for the measurement in said another water content range said first transistor being isolated by said first change-over switch and said second transistor having the base grounded through the first change-over switch and a resistive bias and the emitter connected to a second biasing means through the second change-over switch, thereby to amplify the detected resistance signal.

* * * * *